United States Patent
Hwang (10) Patent No.: US 8,200,305 B2
(45) Date of Patent: Jun. 12, 2012

(54) VARIABLE WAVELENGTH GENERATING METHOD AND APPARATUS THEREOF, FOR USE IN MEASURING BODY FLUIDS CONSTITUENT CONCENTRATION

(75) Inventor: In-duk Hwang, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1807 days.

(21) Appl. No.: 11/176,578

(22) Filed: Jul. 8, 2005

(65) Prior Publication Data

US 2006/0074281 A1 Apr. 6, 2006

(30) Foreign Application Priority Data

Oct. 5, 2004 (KR) .................. 10-2004-0079200

(51) Int. Cl.
*A61B 5/1455* (2006.01)
*F21S 10/02* (2006.01)
(52) U.S. Cl. ........................ 600/310; 362/257
(58) Field of Classification Search .......... 600/309, 600/310, 316, 318, 319, 322, 325, 331, 336, 600/347
See application file for complete search history.

(56) References Cited

U.S. PATENT DOCUMENTS

| | | | |
|---|---|---|---|
| 5,055,684 A | 10/1991 | Honigs | |
| 5,086,229 A | 2/1992 | Rosenthal et al. | |
| 5,209,231 A * | 5/1993 | Cote et al. | 600/310 |
| 5,279,295 A * | 1/1994 | Martens et al. | 600/335 |
| 5,780,867 A | 7/1998 | Fritz et al. | |
| 5,830,132 A * | 11/1998 | Robinson | 600/310 |
| 6,040,578 A | 3/2000 | Malin et al. | |
| 6,253,097 B1 * | 6/2001 | Aronow et al. | 600/310 |
| 6,453,183 B1 * | 9/2002 | Walker | 600/322 |
| 6,522,675 B1 | 2/2003 | Tajima | |
| 6,622,032 B1 * | 9/2003 | Robinson et al. | 600/310 |
| 6,795,453 B2 * | 9/2004 | Pezeshki et al. | 372/20 |
| 7,391,406 B2 * | 6/2008 | Yamamoto et al. | 345/102 |

* cited by examiner

*Primary Examiner* — Eric Winakur
(74) *Attorney, Agent, or Firm* — Staas & Halsey LLP (57) ABSTRACT

A variable wavelength generating method and an apparatus thereof, for use in measuring a body fluid constituent concentration. The apparatus includes: a thermo-electric cooler (TEC) whose temperature is varied depending on a change in a supplied current; a light source section generating a wavelength that is varied depending on a temperature change of the thermo-electric cooler; a current supply control section controlling a current supplied to the TEC; an operation power source generation section supplying an operation power source for performing synchronization so that an operation of the light source section may be performed; and a controller for adjusting a current flowing in the TEC adjusting the operation power source supplied to the light source section.

25 Claims, 9 Drawing Sheets

VARIABLE WAVELENGTH GENERATING METHOD AND APPARATUS THEREOF, FOR USE IN MEASURING BODY FLUIDS CONSTITUENT CONCENTRATION

CROSS-REFERENCE TO RELATED APPLICATION

This application claims the priority of Korean Patent Application No. 10-2004-0079200, filed on Oct. 5, 2004, in the Korean Intellectual Property Office, the disclosure of which is incorporated herein by reference.

BACKGROUND OF THE INVENTION

1. Field of the Invention

The present invention relates to a variable wavelength generating method and an apparatus thereof, for use in measuring body fluid constituent concentration, and more particularly, to a variable wavelength generating method and an apparatus thereof, capable of generating a wavelength of a specific wavelength band in an easy and convenient manner in order to measure a body fluid constituent concentration.

2. Description of Related Art

Recently, as living environments are remarkably improved and life conditions are promoted, interest in individual health is being stressed. Accordingly, lots of research for developing medical implements for home use capable of easily monitoring a health status of an individual several times a day have been carried out and new products are being developed continuously.

In healthy people, body fluid existing inside of the living body is circulated and adjusted organically so that an amount of the body fluid is maintained within in a predetermined range. Examples of such body fluid include blood, urine, interstitial fluid, sweat, and saliva. Particularly, a concentration of a constituent within the body fluid, such as blood, urine (sugar, protein) is a very important variable informing a health status of an individual. Further, a concentration measurement for glucose, hemoglobin, bilirubin, cholesterol, albumin, creatinine, protein, urea existing in an inside of the body fluid is an important object.

However, if the living body gets an illness, a change is generated in a composition or an amount of a body fluid constituent and a dangerous condition may be caused. For example, a blood glucose's concentration of a healthy person is about 80 mg/dl before a meal and 120 mg/dl after a meal. To maintain the blood glucose's concentration, the living body has the pancreas secret an appropriate amount of insulin before and after a meal so that the insulin may be absorbed in the liver and a skeletal muscle cell. However, in case the insulin necessary for maintaining a normal blood glucose is not produced from the pancreas due to a disease or other reason, an excessive amount of glucose gets remained in an inside of blood. Such an excessive glucose remaining in blood may cause a disease in the heart and the liver, arteriosclerosis, high blood pressure, cataract, retinal hemorrhage, nerve injury, hearing loss, and sight deterioration. In a severe case, it may cause a death.

Therefore, it is important to measure a change in the body fluid constituent in an inside of the living body before such an adverse result is caused. For a concentration measurement method for a body fluid constituent, an invasive method for measuring a concentration of a body fluid constituent by directly extracting part of a subject matter and a non-invasive method for performing a measurement without extracting the subject matter. However, since there are lots of problems in the invasive method, a technology for easily diagnosing the body fluid constituent in a non-invasive manner has been being developed. A conventian process for the measurement for a blood glucose has been performed in the following way that blood is extracted to react to a reagent so that results thereof may be used for a clinical analysis or a color change of a test strip that has reacted to a reagent is quantified and used in a diagnosis. When such invasive blood extractions are performed everyday, a painful burden is given to a diabetic and possibility of infection to a disease is increased. Further, since continuous monitoring is hard to perform, it is difficult to take an appropriate measure upon emergence situations. When a strip and a reagent, a great amount of consumables should be used, which gives a burden to a user economically. Further, since the consumables are environment-polluting materials, they should be processed in someway or another. Accordingly, a technology for diagnosing a blood glucose concentration without extracting blood not using a strip or a consumable in order to adjust blood glucose of a diabetic or to perform a medical examination of a healthy people, is highly required.

Spectroscopic methods for use in measuring a concentration of the body fluid constituent within the living body, are mostly a method of illuminating visible light or light of a near infrared (NIR) wavelength region onto part of a living tissue and detecting the light reflected or transmitted therefrom. That is, the method estimates a concentration of the body fluid constituent by mainly measuring its spectrum. For estimation of a specific target constituent concentration, a reference light source of a wavelength band for effectively canceling influence of interfering materials as well as a light source of a wavelength for most readily responding to the constituent to be measured is required.

In the conventional art, a concentration has been computed by measuring a light intensity with an array-type light detector, which is high priced, using a continuous wavelength (CW) lamp light source or by measuring a spectrum with a spectrometer, or a plurality of light emitting diodes (LED) or laser diodes (LD) for generating a specific wavelength have been used.

Since the concentration of the constituent to be measured is very low in blood among the body fluids and a scattering effect of light is very larger than an absorption effect in a biologic tissue and blood, a detected signal is weak, thus a method for amplifying the detected signal is required. Amplification of the detected signal can be achieved by a pulse driving rather than a CW driving of an LD. Since organic matter existing within one living body is constantly flowing, a measurement time should be maintained fast so as to exactly measure a concentration of an organic matter constituent.

Simultaneously, it should be considered that the overall average energy illuminated onto a human body may not exceed a range that causes a damage to a human tissue. Particularly, since an absorption band for glucose is widely distributed in an NIR region ranging from 700 nm to 2500 nm, a glucose absorption peak is relatively small compared to a big aqueous background spectrum, and a small S/N (signal-to-noise ratio) value is shown, exact measurement of a concentration is hard to perform.

The U.S. Pat. No. 5,086,229 entitled "Non-invasive measurement of blood glucose" suggests a method of measuring a glucose concentration within blood in a non-invasive manner, in which: wavelengths of from 600 nm to 1100 nm are used, such wavelengths are obtained using a variety of LEDs, and an energy difference of light transmitted or reflected from a living body is analyzed so that the glucose concentration can be estimated. However, since a great number of LEDs should be combined and used for obtaining a sufficiently strong signal in a glucose absorption wavelength region actually suggested, there is a problem that alignment of LEDs having different wavelengths is not easy. Further, since LEDs having different wavelengths are combined and used, each wavelength is not illuminated onto the same position upon illumination onto a biologic tissue, and thus exact concentration measurement is hard to perform. Still further, there is a problem that the region of from 600 nm to 1100 nm does not include useful glucose information.

The U.S. Pat. No. 6,040,578 entitled "Method and apparatus for multi-spectral analysis of organic blood analytes in noninvasive infrared spectroscopy" relates to an apparatus and a method for measuring a concentration of various blood constituent existing within a living body using a wavelength of from 1100 nm to 5000 nm. Since the above-suggested method detects and analyzes the only light reflected from the living body, a variety of filters is used or a linear array detector is used. However, such a spectrometer, a grating, and an optical element such as a mirror should be used. Accordingly, there exist a fundamental limitation in manufacturing a small-sized product.

The U.S. Pat. No. 5,780,867 entitled "Broadband light-emitting diode" suggests a method for obtaining results by manufacturing III-V group compound semiconductor layers having various energy band-gap in order to generate wide-band wavelengths of from 1.3 μm to 2 μm. However, since a separate spectrometer of a spectroscopic type is additionally required for development of a wavelength variable light source, the commercialized spectrometer of the conventional art can only be used.

BRIEF SUMMARY

An aspect of the present invention provides an apparatus for measuring body fluid constituent concentration in an invasive or a non-invasive manner by easily generating and controlling quasi-continuous wavelength of a predetermined band having an absorption spectrum with respect to the body fluid constituent using a light source section packaged in a small-size and illuminating light of the predetermined wavelength onto a biologic tissue. For that purpose, an aspect of the present invention provides a wavelength adjusting technology that can be effectively varied through a temperature control of a thermo-electric cooler (TEC), which is distinguished from a grating rotation type spectroscopy technology.

According to an aspect of the present invention, there is provided an apparatus for measuring a body fluid constituent concentration, which includes: a variable wavelength generation section generating an optical wavelength signal varied quasi-continuously depending on a temperature change; an optical transmission section illuminating an optical wavelength signal generated from the variable wavelength generation section onto a subject matter whose body fluid constituent concentration is to be measured; an optical reception section detecting an optical wavelength signal transmitted or reflected from the subject matter; a signal processing section processing the optical wavelength signal detected by the optical reception section in a predetermined manner; a constituent concentration analysis/estimation section analyzing and estimating a constituent concentration of the subject matter using spectrum data of the optical wavelength signal obtained by the signal processing section; and a controller providing the optical wavelength signal that has been signal-processed in the predetermined manner to the constituent concentration analysis/estimation section and controlling a temperature change of the variable wavelength generation section.

According to another aspect of the present invention, there is provided a variable wavelength generating apparatus for use in measuring a body fluid constituent concentration, which includes: a thermoelectric cooler whose temperature is varied depending on a change in a supplied current; a light source section mounted on an upper portion of the thermo-electric cooler, generating light having wavelength that is varied depending on a temperature change of the thermo-electric cooler; a current supply control section controlling a current supplied to the thermo-electric cooler; an operation power source generation section supplying an operation power source performing synchronization so that an operation of the light source section may be performed; and a controller adjusting a current flowing in the thermoelectric cooler by controlling the current supply control section and adjusting the operation power source supplied to the light source section by controlling the operation power source generation section.

According to a another aspect of the present invention, there is provided a method for measuring a body fluid constituent concentration, which includes: generating a wavelength varied quasi-continuously by a temperature change; illuminating an optical wavelength signal generated from the generating operation onto a subject matter whose body fluid constituent concentration is to be measured; detecting an optical wavelength signal transmitted or reflected from the subject matter; processing the detected optical wavelength signal; and analyzing and estimating a body fluid constituent concentration of the subject matter using spectrum data of the processed optical wavelength signal obtained.

According to a still another aspect of the present invention, there is provided a variable wavelength generating method for use in measuring a body fluid constituent concentration in a system for measuring a body fluid constituent concentration having a light source section on the thermo-electric cooler (TEC), which includes: adjusting a temperature of the thermo-electric cooler by controlling a current supplied to the thermo-electric cooler; supplying an operation power source for synchronizing the light source section; and generating light having an optical wavelength varied depending on a temperature of the adjusted thermo-electric cooler.

According to other aspects of the present invention, there are provided computer-readable storage media encoded with processing instructions for causing a processor to perform methods according to the above-described aspects of the present invention.

According to a still another aspect of the present invention, there is provided a apparatus for measuring fluid constituent concentration, which includes: a variable wavelength generator generating an optical wavelength signal of a variable wavelength; an optical transmitter transmitting the generated optical wavelength signal onto a subject matter the fluid concentration of which is to be measured; an optical receiver receiving the optical wavelength signal reflected from the subject matter; and a constituent concentration analyzer/estimator analyzing and estimating a fluid constituent concentration of the subject matter based on the received optical wavelength signal.

Additional and/or other aspects and advantages of the present invention will be set forth in part in the description which follows and, in part, will be obvious from the description, or may be learned by practice of the invention.

BRIEF DESCRIPTION OF THE DRAWINGS

These and/or other aspects and advantages of the present invention will become apparent and more readily appreciated from the following detailed description, taken in conjunction with the accompanying drawings of which.

DETAILED DESCRIPTION OF EMBODIMENTS

Reference will now be made in detail to embodiments of the present invention, examples of which are illustrated in the accompanying drawings, wherein like reference numerals refer to the like elements throughout. The embodiments are described below in order to explain the present invention by referring to the figures.

Figure 1:
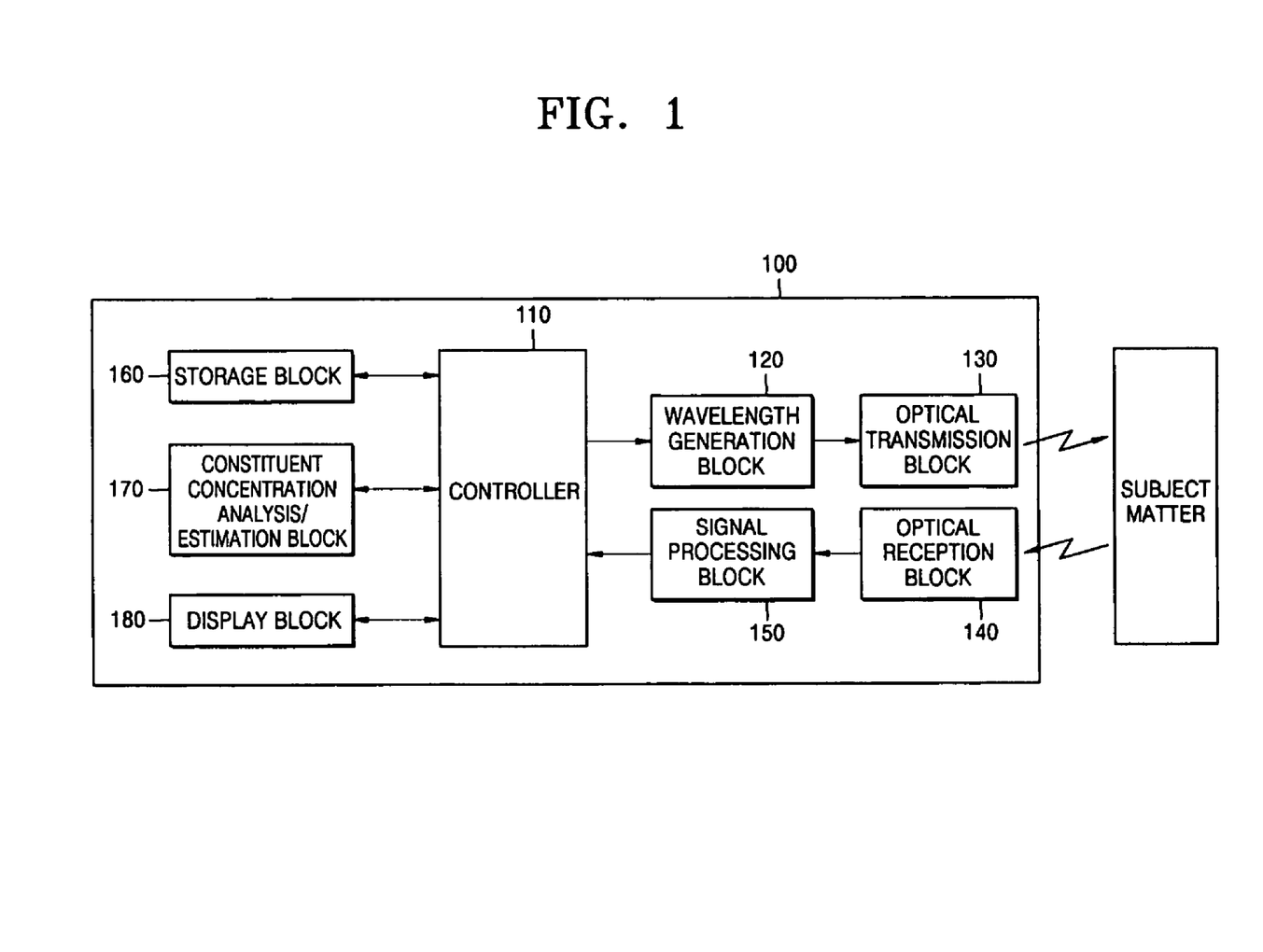
FIG. 1 is a block diagram of an apparatus for measuring a body fluid constituent concentration according to an embodiment of the present invention.
Figure 2:
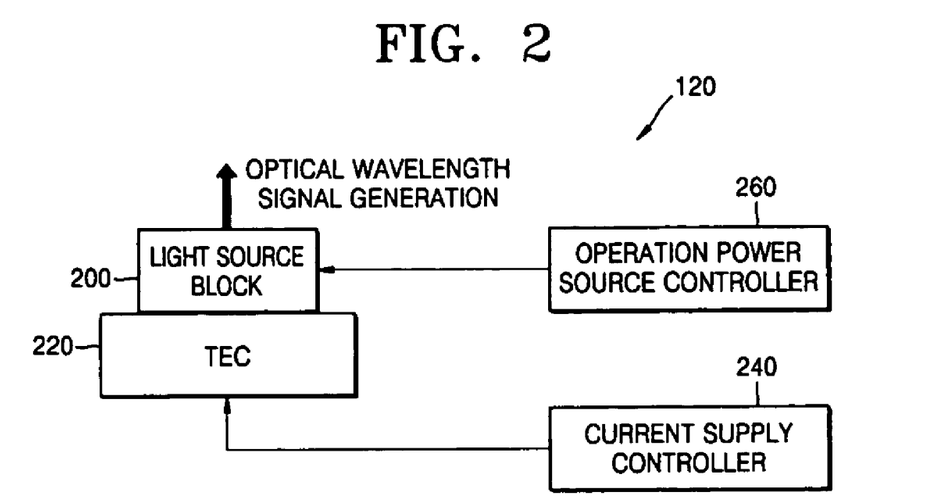
FIG. 2 is a block diagram illustrating a variable wavelength generation section of FIG. 1 in more detail.
Figure 3:
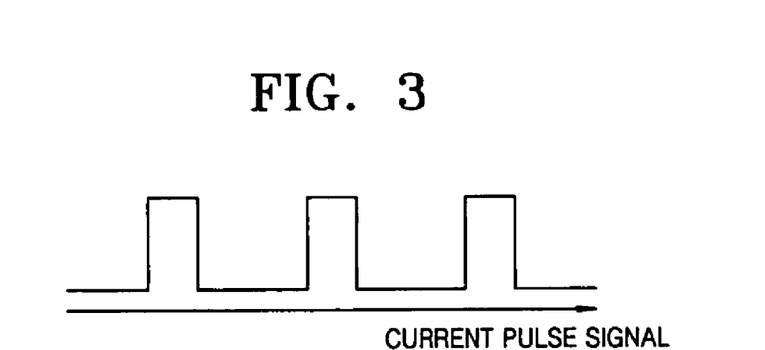
FIG. 3 is a view illustrating an operation power source generated from the variable wavelength generation section of FIG. 1.
Figure 4:
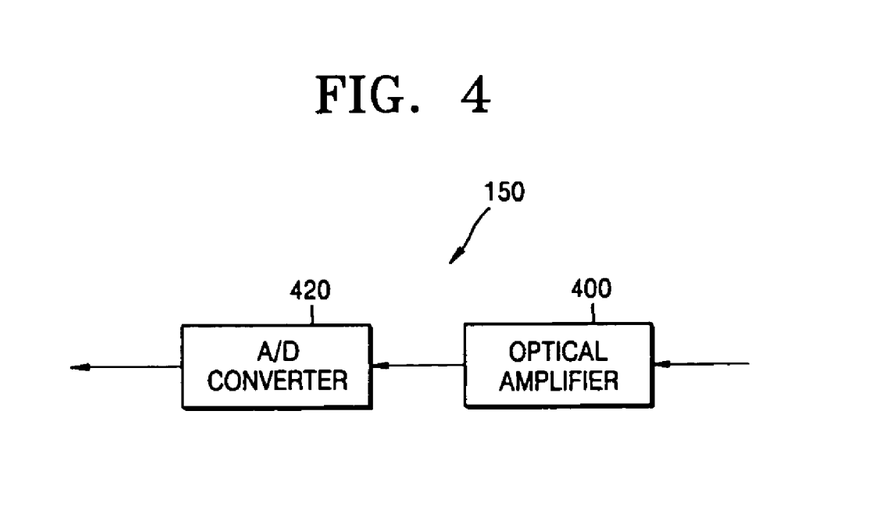
FIG. 4 is a block diagram illustrating a signal processing section of FIG. 1 in more detail.

FIG. 1 is a block diagram of an apparatus for measuring a body fluid constituent concentration according to an embodiment of the present invention, FIG. 2 is a block diagram illustrating a variable wavelength generation section of FIG. 1 in more detail, FIG. 3 is a view illustrating an operation power source generated from the variable wavelength generation section of FIG. 1, and FIG. 4 is a block diagram illustrating a signal processing section of FIG. 1 in more detail.

Referring to FIG. 1, a variable wavelength generating apparatus for use in measuring a body fluid constituent concentration includes: a variable wavelength generation section 120 for generating a predetermined variable wavelength; an optical transmission section 130 for illuminating the optical wavelength signal generated from the variable wavelength generation section 120 onto a subject matter whose body fluid constituent concentration is to be measured; an optical reception section 140 for detecting (receiving) the optical wavelength signal transmitted or reflected from the subject matter; a signal processing section 150 for processing the optical wavelength signal detected by the optical reception section 140 in a predetermined manner so as to transmit the optical wavelength signal to a controller 110; a storage section 160 where each reference spectrum data for a body fluid constituent concentration is stored; a constituent concentration analysis/estimation section 170 for analyzing and estimating a constituent concentration of the subject matter by comparing the reference spectrum data for a body fluid constituent concentration stored in the storage section 160 with spectrum data of the optical wavelength signal obtained by the signal processing section 150; and a display section 180 for displaying so that a user may understand analysis/estimation data estimated by the constituent concentration analysis/estimation section 170.

Referring to FIG. 2, the variable wavelength generation section 120 of FIG. 1 includes: a light source section 200 (e.g., an LD) packaged in a several mm×mm structure on a thermo-electric cooler 220 (TEC); an operation power source controller 260 for supplying an operation power source to the light source blosectionck 200 to operate the light source section 200; and a current supply controller 240 for sequentially controlling a temperature by controlling a current supplied to the TEC 220 in order to generate a wavelength varied depending on a temperature.

The variable wavelength generation section 120 will be described in more detail with reference to FIGS. 1 and 2.

If light is illuminated onto a subject matter (e.g., a target (biologic) tissue), the illuminated light is transmitted or reflected from the subject matter. The light reflected from the subject matter is guided by an optical system (e.g., a lens, a mirror, or a combination of them) and received as an optical wavelength signal to the optical reception section 140, where the received optical wavelength signal is changed into an analog signal.

The optical wavelength signal received from the optical reception section 140 is signal-processed in a predetermined manner at the signal processing section 150. Here, the signal processing is performed in such a way that an optical signal inputted as an analog signal is provided to the controller 110 so that a constituent concentration may be analyzed and estimated. More specifically, the signal processing performed at the signal processing section 150 is performed in the following way with reference to FIG. 4, in which: an optical wavelength signal received from the optical reception section 140 is amplified at an optical amplifier (pre-Amp) 400, and the amplified optical wavelength signal is converted into a digital optical wavelength signal at an analog/digital converter (A/D converter) 420 so that a signal processing may be possible at the controller 110 (e.g., a microcomputer).

The controller 110 is provided with the digital optical wavelength signal outputted from the A/D converter 420 and transmits the same to the constituent concentration analysis/estimation section 170.

The constituent concentration analysis/estimation section 170 loads reference spectrum data regarding each subject constituent within the body fluid, stored in the storage section 160 and analyzes and estimates a subject matter's constituent concentration within the body fluid, to be measured on the basis of spectrum data of a digital optical wavelength signal inputted from the controller 110. More specifically, the constituent concentration analysis/estimation section 170 compares an intensity of an absorption degree for each optical wavelength used in measurement with the reference spectrum data using an estimation model formula estimating an exact concentration regarding the body fluid constituent, thereby computing an exact concentration regarding the body fluid constituent. Here, for a statistical analysis for use in concentration estimation, a variety of conventional analysis methods may be used such as various multivariate methods including partial least square (PLS), principal component regression (PCR), multiple linear regression (MLR), and nonlinear PLS.

Referring to FIG. 2, the light source section 200 manufactured on the TEC 220 is formed in form of a module. The current supply controller (current supply control section) 240 controls a current applied to the TEC 220 so that a temperature of the TEC 220 may be varied. If a temperature of the TEC 220 is varied, a wavelength A generated at the light source section 200 mounted on the TEC 220 is varied.

Referring to FIGS. 1 and 3, the light source section 200 operates synchronized with a current pulse signal supplied from the operation power source controller 260. Since the operation power source is supplied in synchronization as described above, it is possible to improve a S/N value even if an outputted optical wavelength signal is considerably small. The current supply controller 240 and the operation power source controller (operation power source control section) 260 are under control of the controller 110.

In association with mounting the light source section 200 on the TEC 220, a variety of embodiments may be possible. Though the light source section 200 may include only one light source element, it is preferred that the light source section 200 includes a plurality of light source elements. The light source element can be realized using a light emitting diode (LED) or a laser diode (LD).

A plurality of light source elements may be configured such that characteristics of the light source elements are different each other. That is, light source elements such that optical wavelengths generated under the same temperature are different each other may be used. In association with preparing a plurality of light source elements, first, the plurality of light source elements may be configured such that each of the light source elements is mounted on the TECs 220 so formed as to correspond, one by one, to each of the plurality of light source elements. Second, the plurality of light source elements may be configured to be mounted together on one single TEC 220.

In the above first case, the current supply controller 240 is connected with each of the TECs 220 so that a current flowing in each of the TECs 220 may be controlled and temperatures of the TECs 220 may be different each other. It is also possible to control the temperatures of the TECs 220 to be the same each other.

In the above second case, the current supply controller 240 is connected with the TEC 220 to control a current flowing in the TEC 220, thereby controlling a temperature of the TEC 220.

In case of constructing a plurality of light source elements as described above, the operation power source controller 260 is connected with each of light source elements of the light source section 200 so as to generate an operation power source signal to operate each of the light source elements with a predetermined time interval or with a predetermined period. Here, the operation power source controller 260 may control the operation power source by generating a current clock signal.

Referring to FIG. 2, the variable wavelength generation section 120 does not use a spectrometer (spectroscopy method) widely used in the conventional art, having a light source, an optical part, a scan-type grating, but directly forms the packaged light source section on the TEC 220 to control a temperature of the TEC 220, thereby having a different wavelength outputted from the light source section 200. The light source section 200 includes a plurality of light source elements and the operation power source controller 260 supplies an operation power source supplied to each of the light source elements with a predetermined time interval, so that various wavelengths generated from the light source section 200 are sequentially generated and wavelengths of a specific wide band can be generated. Since each constituent of a subject matter circulates within the subject matter as time flows, a wavelength generation time and a measuring time should be shortened so that measurement difficulty due to circulation of the constituent as time flows can be minimized.

The light source section 200 may mount a plurality of light source elements on the TEC 220 and the current supply controller 240 controls a current supplied to the TEC 220 so that a specific wavelength band may be generated by a plurality of light source elements. Accordingly, the variable wavelength generation section 120 can be used in measuring a constituent concentration existing in the body fluid in an invasive or a non-invasive manner.

For example, for measurement of glucose concentration, a wide band spectrum including a wavelength band where great absorption occurs with respect to glucose and a wavelength band where small absorption occurs, is generated, and the generated wavelengths are illuminated onto a living body, and then reflected or transmitted optical wavelength signals are analyzed and estimated in viewpoint of an absorption difference for each optical wavelength received from the optical reception section 140, so that glucose concentration of a constituent in blood can be exactly estimated.

Figure 5A:
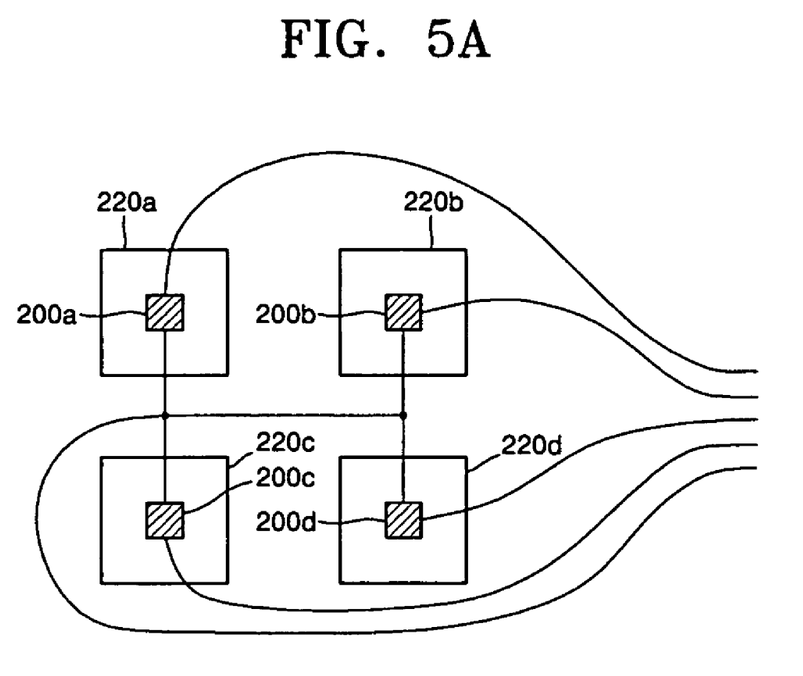
FIGS. 5A and 5B are respective schematic and plan views of a construction of the variable wavelength generation section of FIG. 1.
Figure 5B:
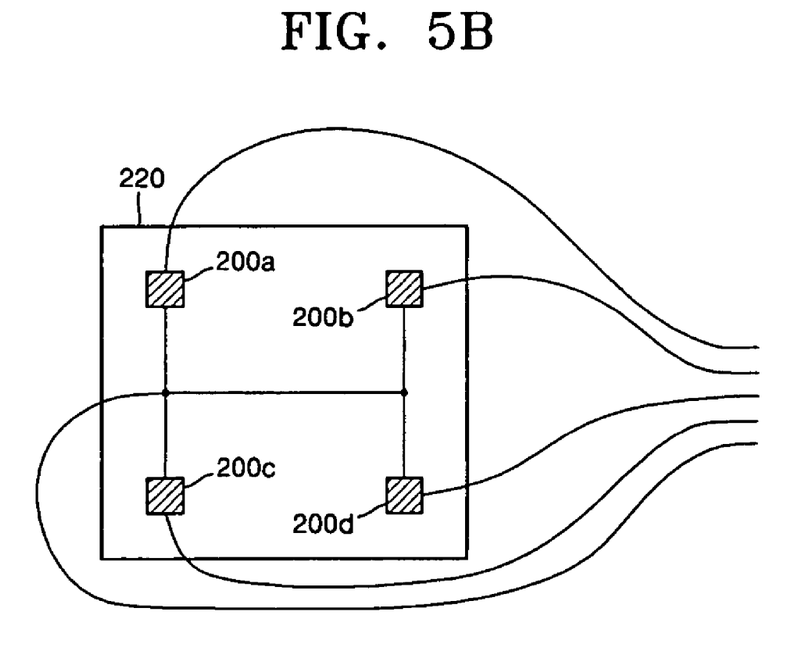

FIGS. 5A and 5B are respective schematic and plan views of a construction of the variable wavelength generation section 120 of FIG. 1.

Referring to FIGS. 1, 2, and 5A, respective four light source elements 200a, 200b, 200c, and 200d are respectively mounted on respective four TECs 220a, 220b, 220c, and 220d. Here, a current supplied to each of the TECs 220 through the current supply controller 260 is varied and a temperature is controlled so that a variable wavelength may be generated from the light source elements of the light source section 200. Particularly, the controller 110 can control the current supply controller 260 to control a current supplied to each of the TECs 220. More specifically, the controller 110 can control in such a way that: a current 1A, a current 2A, a current 3A, and a current 4A (not shown) are supplied to a TEC 220a, a TEC 220b, a TEC 220c, and a TEC 220d, respectively.

Referring to FIG. 5B, four light source elements 200a, 200b, 200c, and 200d, respectively, are mounted on the TEC 220. Here, a current supplied to the TEC 220 through the current supply controller 260 is varied and a temperature is controlled so that a variable wavelength may be generated from the light source elements of the light source section 200. The controller 110 controls a current supplied from the current supply controller 260 to the TEC 220.

Although the four light source elements 200a, 200b, 200c, and 200d are illustrated as mounted on the TEC 220 in FIGS. 5A and 5B, various modifications in a number of light source elements formed on the light source section 200 may be possible. Thus, it is to be understood that the light source section 200 may have one light source element and may have a plurality of light source elements.

Figure 6A:
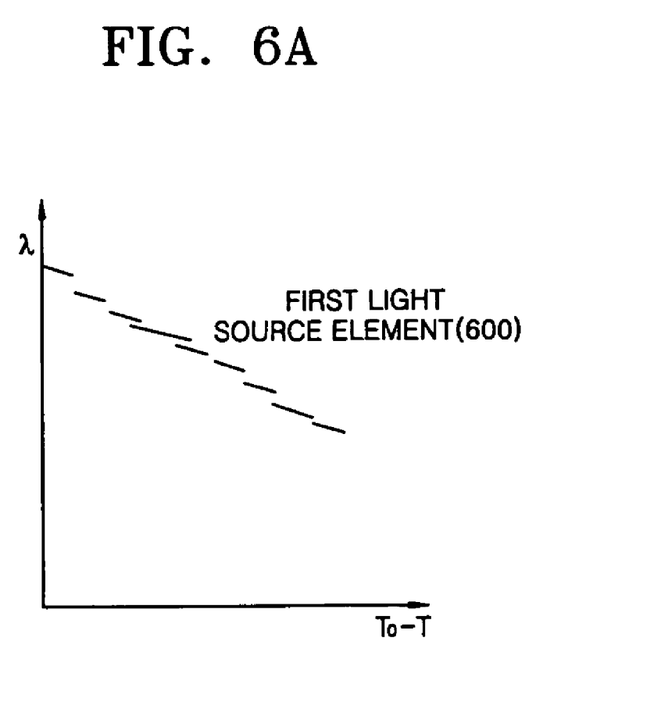
FIGS. 6A and 6B are graphs illustrating that a wavelength generated from a light source section is varied depending on a temperature change of a thermo-electric cooler of FIG. 2.
Figure 6B:
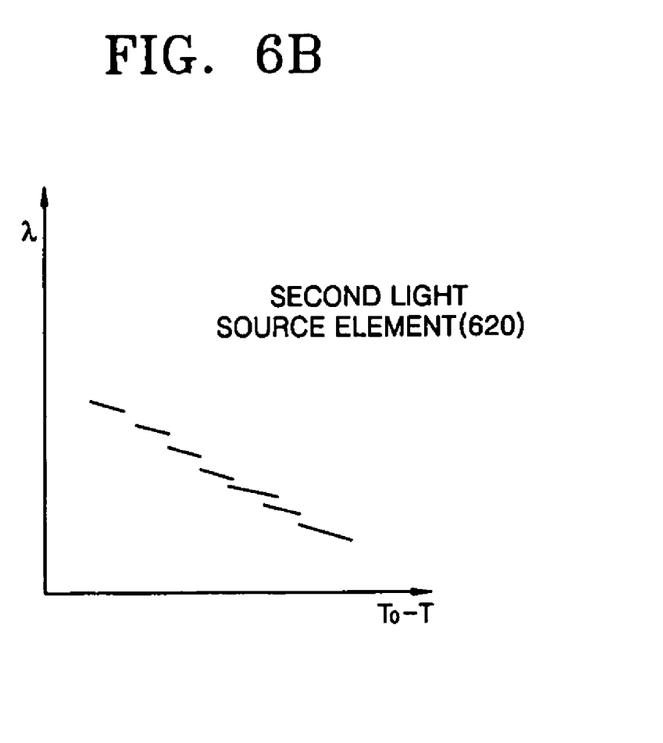

FIGS. 6A and 6B are graphs illustrating that a wavelength generated from the light source section is varied depending on a temperature change of the TEC of FIG. 2.

Referring to FIGS. 2, 6A and 6B, a degree of a wavelength variation with respect to the light source element, which is an element of the packaged light source section 200, is shown. That is, a current supplied to the TEC 220 where a first light source element (e.g., first LD) 600 and a second light source element (e.g., second LD) 620 whose primary wavelengths are different but having a predetermined wavelength band-with (e.g., 100 nm), is mounted, is changed to change a temperature, so that wavelengths generated at the first and the second light source elements 600 and 620 are generated quasi-continuously. In FIGS. 6A and 6B, the horizontal axis represents a temperature change of the TEC 220 and the vertical axis represents wavelengths respectively generated at the first and the second light source elements 600 and 620 depending on a temperature change of the TEC 220.

Figure 7A:
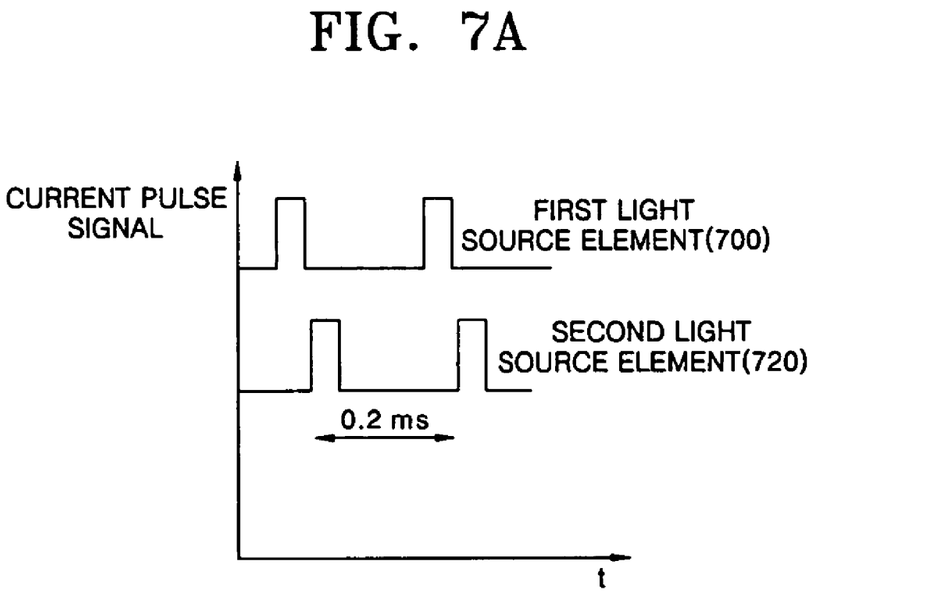
FIGS. 7A and 7B are graphs illustrating that a wavelength generated from a light source section is varied depending on time synchronization of a current pulse signal supplied to a light source element of FIG. 2.
Figure 7B:
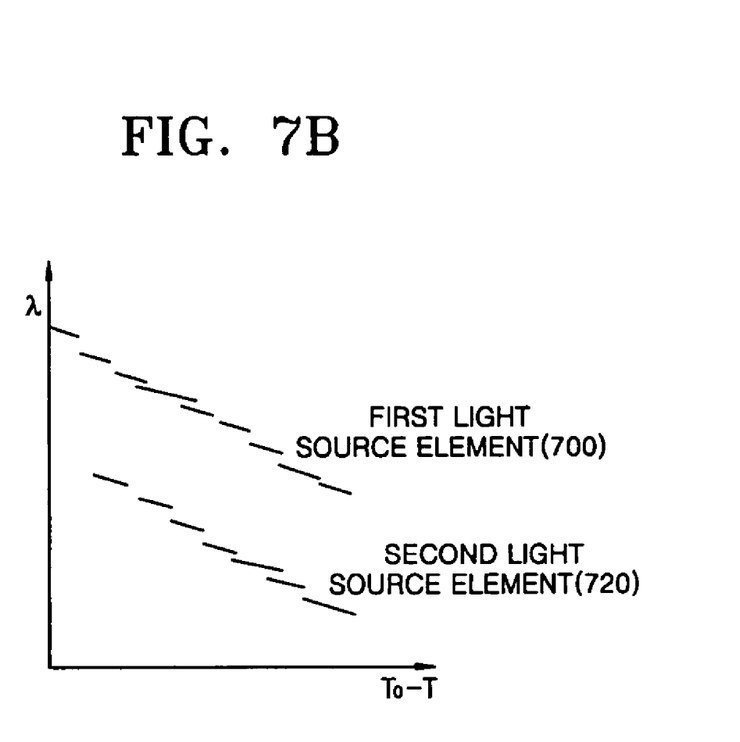

FIGS. 2, 7A and 7B are graphs illustrating that a wavelength generated from a light source section is varied depending on time synchronization of a current pulse signal supplied to a light source element of FIG. 2.

Referring to FIG. 7A, a current pulse signal generated at the operation power source controller 260 and supplied to a first and a second light source elements 700 and 720 has a predetermined period (0.2 ms) and a time difference. If a current pulse signal is supplied to the first and the second light source elements 700 and 720 with a predetermined period and a time difference, the first and the second light source elements 700 and 720 generate optical wavelength signals of different wavelengths with a time difference under a predetermined temperature as shown in FIG. 7B.

Figure 8:
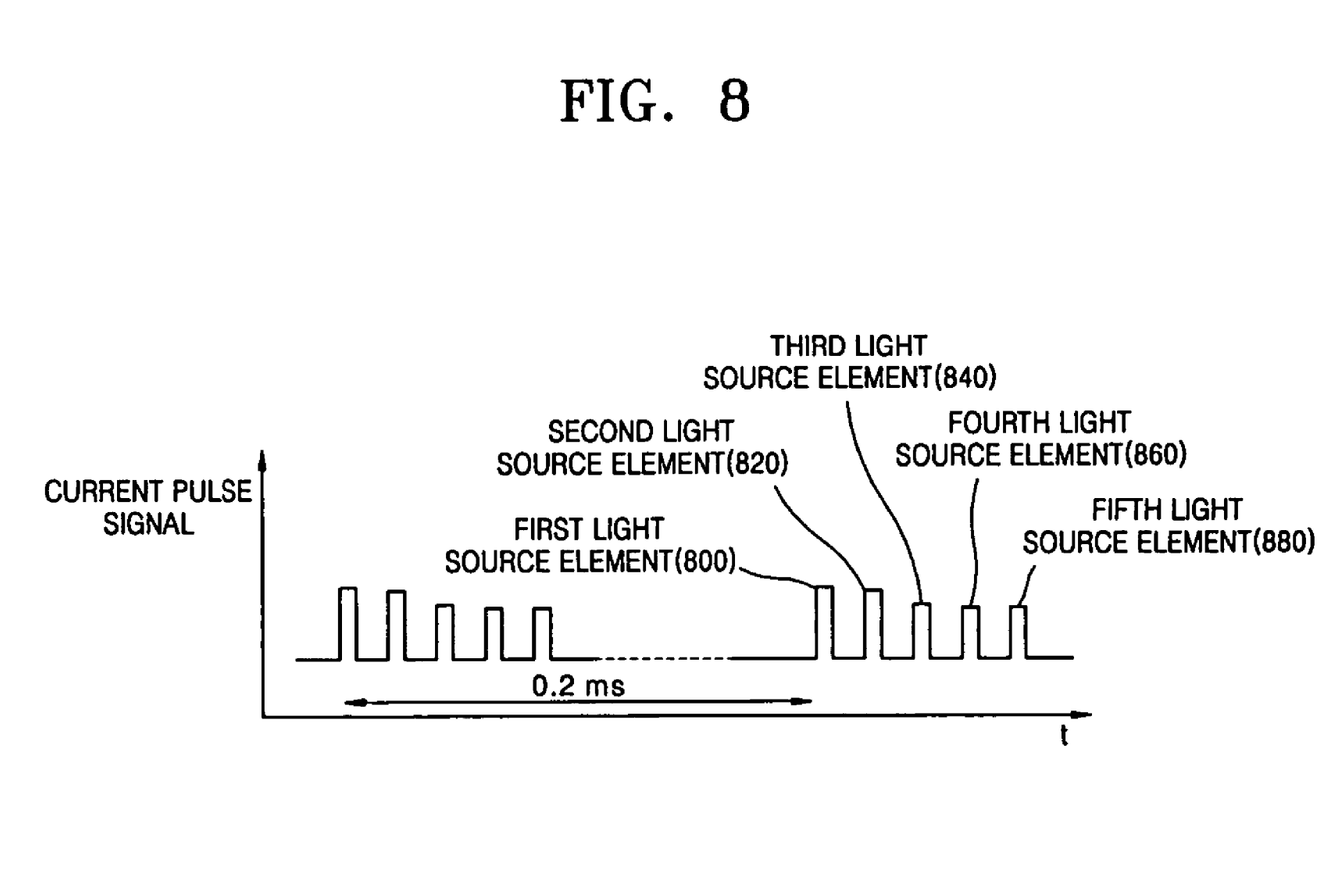
FIG. 8 is a graph illustrating another example of a time difference of a current pulse signal supplied to a plurality of light source elements.

FIG. 8 is a graph illustrating another example of a time difference of a current pulse signal supplied to a plurality of light source elements.

Referring to FIGS. 2 and 8, current pulse signals generated at the operation power source controller 260 and flowing in each of the five light source elements 800, 820, 840, 860, and 880, have a predetermined period (0.2 ms) and a time difference.

Figure 9:
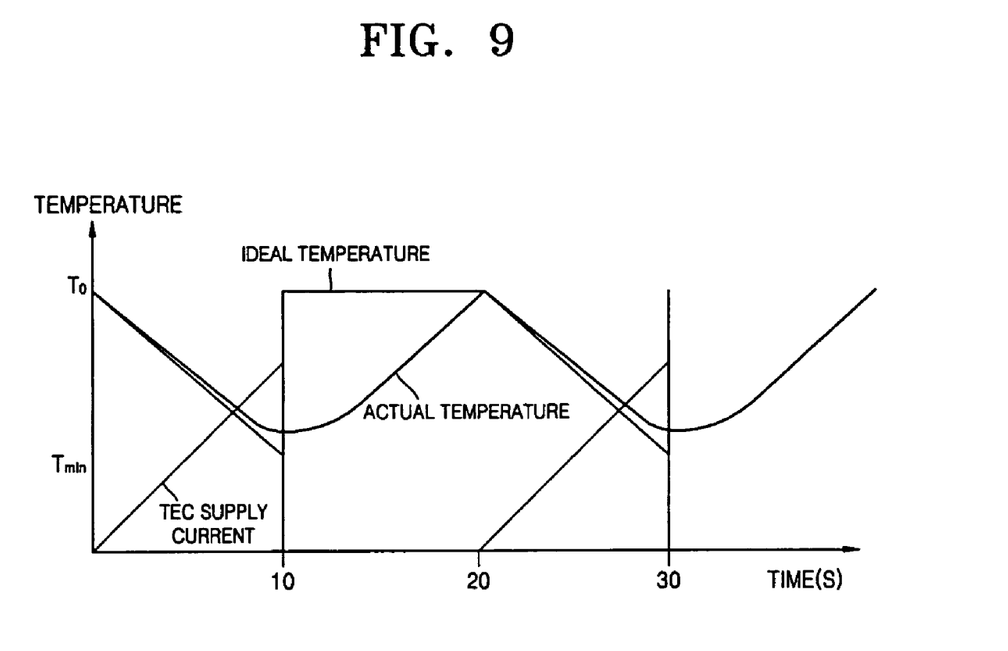
FIG. 9 is a graph illustrating an actual temperature change in the thermoelectric cooler in case a periodically changing operation power source is supplied to the thermo-electric cooler of FIG. 2.

FIG. 9 is a graph illustrating an actual temperature change in the TEC in case a periodically changing operation power source is supplied to the TEC of FIG. 2.

Referring to FIGS. 2 and 9, in case a power source (a current in FIG. 9) supplied to the TEC 220 is supplied with a predetermined period, a relation of an ideal temperature change in the TEC 220 and an actual temperature change is shown. Even if a current supplied to the TEC 220 is supplied with a predetermined period, actually a temperature of the TEC is not changed fast into an initial status in real time at a big changing region (from maximum to minimum in a period) of a supplied current, but gradually changed. In case of a fast body fluid constituent measurement, a temperature should be promptly varied without a predetermined recovery time depending on a current change period of the TEC 220.

Figure 10:
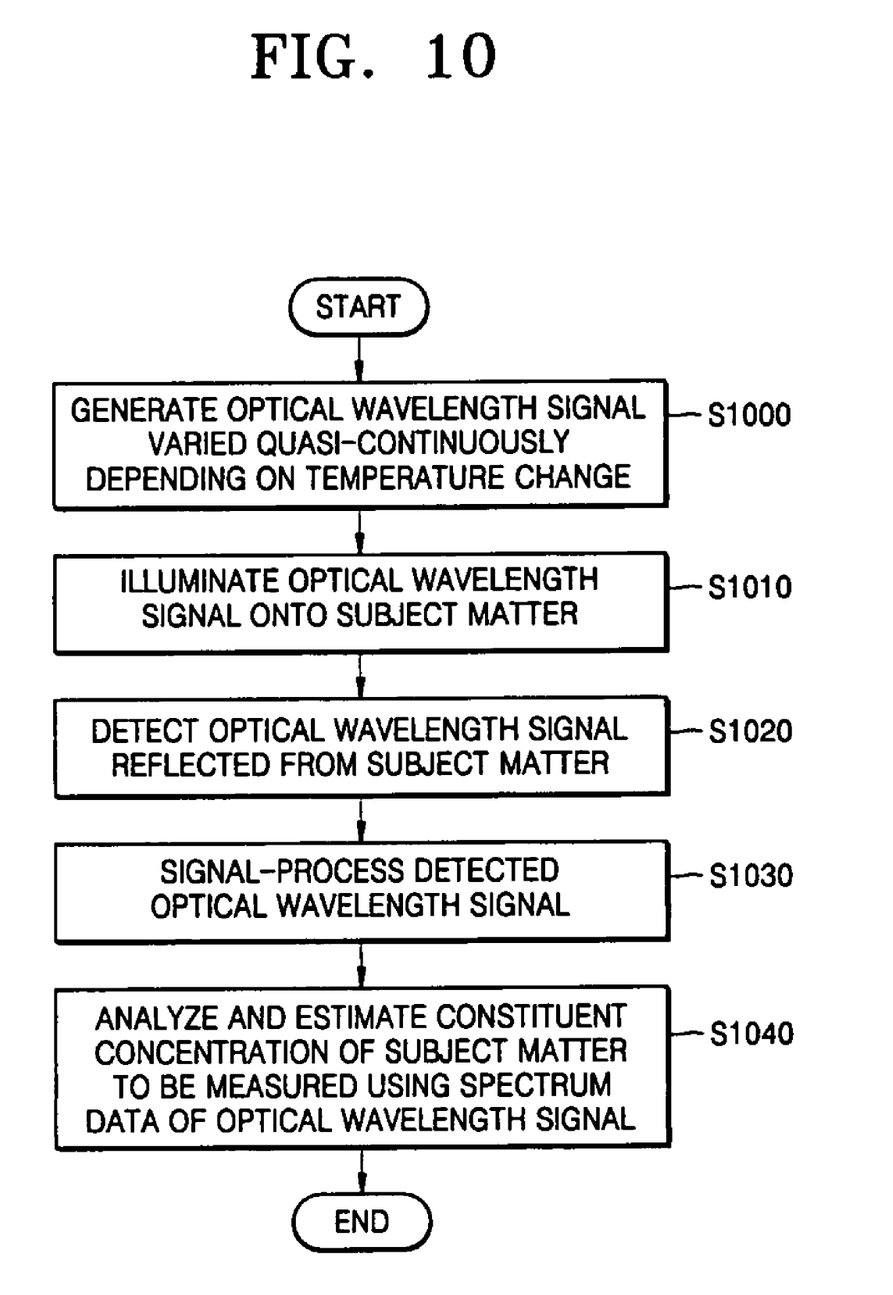
FIG. 10 is a flowchart of a method for measuring a body fluid constituent concentration according to an embodiment of the present invention.

FIG. 10 is a flowchart of a method for measuring a body fluid constituent concentration according to an embodiment of the present invention.

First, an optical wavelength signal varied quasi-continuously depending on a temperature change is generated (S1000).

Next, the varied optical wavelength signal is illuminated onto a subject matter whose body fluid constituent concentration is to be measured (S1010).

After that, an optical wavelength signal transmitted or reflected from the subject matter is detected (S1020).

Then, a predetermined signal processing is performed for the detected optical wavelength signal (S1030). Here, during the signal processing, the detected optical wavelength signal is optically amplified and the optically amplified signal is converted into a digital signal.

Next, spectrum data of the optical wavelength signal is obtained from the optical wavelength signal obtained in the operation S1030 and the body fluid constituent concentration of the subject matter is analyzed and estimated using the spectrum data (S1040). For parts not explained in FIG. 10, refer to the parts related to the apparatus for measuring the body fluid constituent concentration described in the above.

Figure 11:
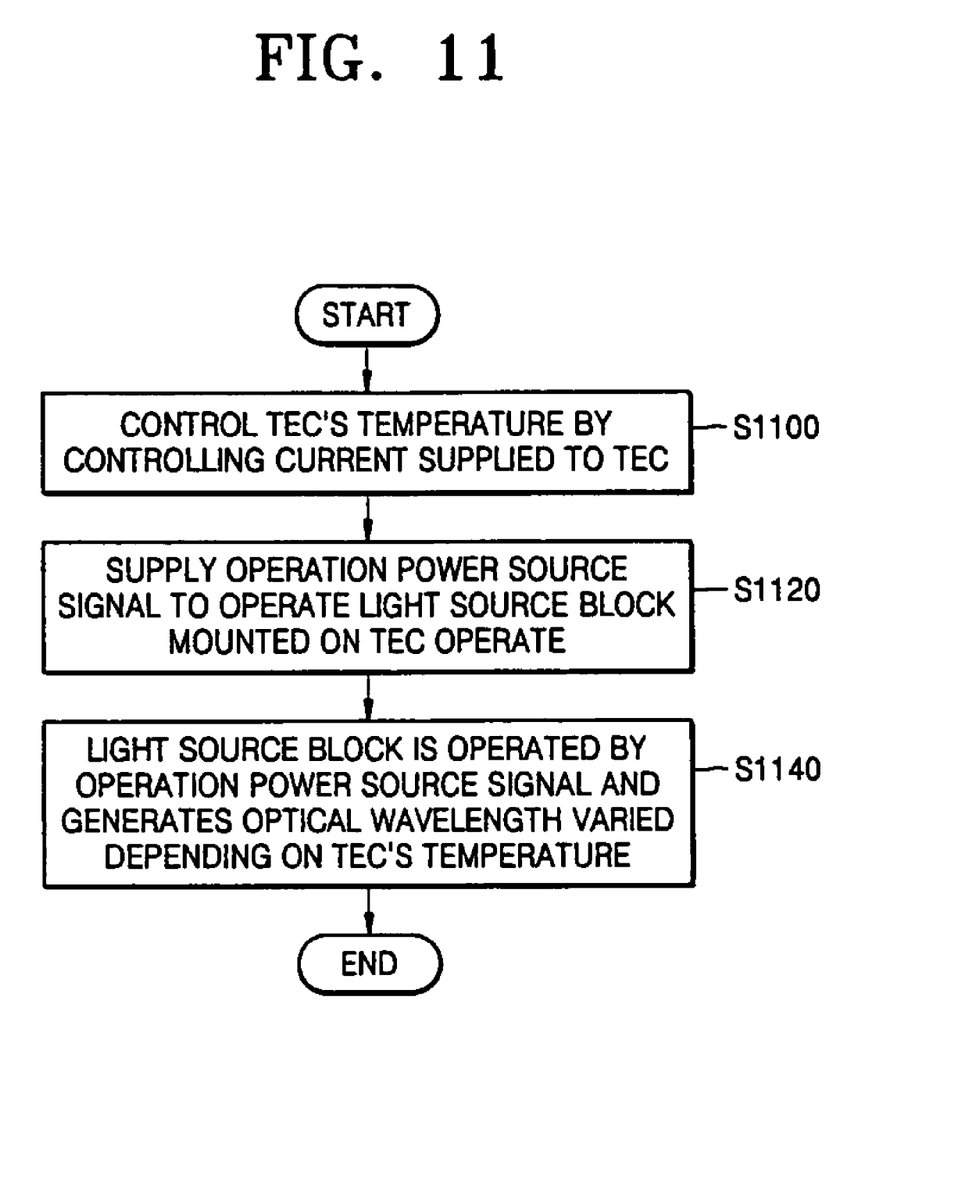
FIG. 11 is a flowchart of a variable wavelength generation method for use in measuring body fluid constituent concentration according to an embodiment of the present invention.

FIG. 11 is a flowchart of a variable wavelength generation method for use in measuring body fluid constituent concentration according to an embodiment of the present invention.

First, in a system for measuring body fluid constituent concentration in which a light source section is mounted on the TEC, a current supplied to the TEC is controlled so that a temperature of the TEC is controlled (S1100).

Next, an operation power source for operating the light source section is supplied (S1120).

Then, the light source section generates an optical wavelength varied depending on a temperature of the TEC controlled in the operation S1100 (S1140). Parts not explained in FIG. 11, refer to the parts related to a variable wavelength generation apparatus for use in measuring body fluid constituent concentration described above.

The above-described embodiments of the present invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices. The computer readable recording medium can also be distributed over network coupled computer systems so that the computer readable code is stored and executed in a distributed fashion.

The above-described embodiments of the present invention has the following effects.

It is possible to provide a simple type, small-sized apparatus for measuring a body fluid constituent concentration using a variable wavelength generating apparatus capable of measuring the body fluid constituent concentration in an invasive or a non-invasive manner.

The above-described embodiments of the present invention can be utilized in measuring the body fluid constituent requiring a specific variable wavelength band and can generate a variable wavelength using a assembly packaged in a small size.

Further, since small-sizing/light weight is possible due to a rapid improvement of a micro-electromechanical systems (MEMS) manufacturing technology of an optical element, compact-sizing of the whole apparatus for measuring body fluid constituent is possible. Still further, since a pulse driving can obtain a larger power than the CW driving, a S/N value can be improved.

Another still further, the variable wavelength generating apparatus for use in measuring a body fluid constituent concentration can be applied to various similar application systems besides the body fluid constituent concentration measurement.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An apparatus for measuring a body fluid constituent concentration, comprising:
    a variable wavelength generation section generating varying optical wavelength signal, varying depending on a temperature change, by using a plurality of light source elements;

an optical transmission section configured to illuminate the varying optical wavelength signal generated from each of the light source elements onto a subject matter whose body fluid constituent concentration is to be measured;

an optical reception section configured to detect the varying optical wavelength signal transmitted or reflected from the subject matter; and a constituent concentration analysis/estimation section analyzing and estimating a constituent concentration of the subject matter using the varying optical wavelength signal detected by the optical reception section.

2. The apparatus of claim 1, wherein the variable wavelength generation section includes:

a thermo-electric cooler (TEC) whose temperature is varied depending on a change in a supplied current;

a light source section generating a wavelength that is varied depending on a temperature change of the TEC by using the light source elements; and a current supply controller controlling a current supplied to the TEC.

3. The apparatus of claim 2, wherein the variable wavelength generation section includes an operation power source controller supplying an operation power source signal to the light source section.

4. The apparatus of claim 1, further comprising a storage section storing reference spectrum data regarding the body fluid constituent concentration, and wherein the constituent concentration analysis/estimation section extracts spectrum data of the varying optical wavelength signal detected by the optical reception section and compares the extracted spectrum data with the reference spectrum data regarding the body fluid constituent concentration stored in the storage section, thereby estimating the body fluid constituent concentration of the subject matter.

5. The apparatus of claim 1, further comprising a display section displaying body fluid constituent concentration analysis/estimation data of the subject matter, analyzed and estimated by the constituent concentration analysis/estimation section.

6. The apparatus of claim 1, further comprising a signal processing section having an optical amplifier amplifying the varying optical wavelength signal detected by the optical reception section and an analog/digital (A/D) converter for the varying optical wavelength signal amplified by the optical amplifier into a digital optical wavelength signal.

7. A variable wavelength generating apparatus, comprising:

a thermoelectric cooler (TEC) whose temperature is varied depending on a change in a supplied current;

a light source section generating an optical wavelength signal that varies depending on a temperature change of the TEC, by using a plurality of light source elements;

a current supply controller configured for controlling a current supplied to the TEC for controlling the varying of the optical wavelength signal; and an operation power source generation section supplying an operation power source signal to operate the light source section.

8. The apparatus of claim 7, wherein the light source section is configured such that the light source elements are mounted in form of a module on the TEC.

9. The apparatus of claim 8, wherein the operation power source generation section supplies operation power source signals to each of the light source elements so that each of the light source elements operates with a predetermined period and a predetermined time difference.

10. The apparatus of claim 9, wherein the operation power source generation section includes a time delay device by which the operation power source generation section supplies the operation power source signal to each of the light source elements with a time difference.

11. The apparatus of claim 8, wherein each of the light source elements included in the light source section is mounted on a single-type TEC.

12. The apparatus of claim 8, wherein the TEC is formed in plural elements so that each of the elements of the TEC is connected with each of the light source elements included in the light source section.

13. The apparatus of claim 7, wherein the operation power source signal is a current pulse signal having a predetermined period.

14. The apparatus of claim 7, wherein the light source section includes a light emitting diode (LED) or a laser diode (LD).

15. A method of measuring a body fluid constituent concentration, comprising:

generating a varying optical wavelength signal, varying depending on a temperature change, by using a plurality of light source elements;

illuminating the generated varying optical wavelength signal onto a subject matter whose body fluid constituent concentration is to be measured;

detecting the varying optical wavelength signal transmitted or reflected from the subject matter; and analyzing and estimating a body fluid constituent concentration of the subject matter using the detected optical wavelength signal.

16. The method of claim 15, further comprising, between the detecting and the analyzing, loading reference spectrum data regarding a body fluid constituent concentration, and wherein the analyzing extracts spectrum data of the detected varying optical wavelength signal and compares the extracted spectrum data with the stored reference spectrum data, thereby estimating a body fluid constituent concentration of a subject matter.

17. The method of claim 15, further comprising, between the detecting and the analyzing, amplifying the detected varying optical wavelength signal and converting the amplified varying optical wavelength signal into a digital optical wavelength signal.

18. The method of claim 15, further comprising displaying analyzed and estimated body fluid constituent concentration analysis/estimation data of the subject matter.

19. A variable wavelength generating method for use in measuring a body fluid constituent concentration in a system having a light source section on its thermo-electric cooler (TEC), the method comprising:

adjusting a temperature of the TEC by controlling a current supplied to the TEC;

supplying an operation power source operating the light source section; and generating, at the light source section, a varying optical wavelength signal, varying depending on an adjusted temperature of the TEC, by using a plurality of light source elements.

20. The method of claim 19, wherein the light source section is configured such that the light source elements are mounted in form of a module on the TEC.

21. The method of claim 20, wherein the supplying supplies operation power sources to each of the light source elements so that each of the light source elements can operate with a predetermined period and a predetermined time difference.

22. A non-transitory computer readable medium comprising a computer readable computer program code to control at least one processing device to execute a method of measuring a body fluid constituent concentration, the method comprising:
- generating a varying optical wavelength signal, varying depending on a temperature change, by using a plurality of light source elements;
- illuminating the generated varying optical wavelength signal onto a subject matter whose body fluid constituent concentration is to be measured;
- detecting the varying optical wavelength signal transmitted or reflected from the subject matter; and
- analyzing and estimating a body fluid constituent concentration of the subject matter using the detected optical wavelength signal.

23. A non-transitory computer readable medium comprising a computer readable computer program code to control at least one processing device to execute a method of a variable wavelength generating method for use in measuring a body fluid constituent concentration in a system having a light source section on its thermo-electric cooler (TEC), the method comprising:
- adjusting a temperature of the TEC by controlling a current supplied to the TEC;
- supplying an operation power source operating the light source section; and
- generating, at the light source section, a varying optical wavelength signal, varying depending on an adjusted temperature of the TEC, by using a plurality of light source elements,
- wherein each of the light source elements generate the varying optical wavelength signal by depending on the temperature change.

24. An apparatus for measuring fluid constituent concentration, comprising:
- a variable wavelength generator generating a varying optical wavelength signal by using at least one of a light source element;
- an optical transmitter transmitting the generated varying optical wavelength signal onto a subject matter the fluid concentration of which is to be measured;
- an optical receiver receiving the varying optical wavelength signal reflected from the subject matter; and
- a constituent concentration analyzer/estimator analyzing and estimating a fluid constituent concentration of the subject matter based on the received optical wavelength signal,
- wherein the one light source element generates the varying optical wavelength signal by depending on the temperature change.

25. The apparatus of claim 24, wherein the wavelength of the optical wavelength signal is controlled to vary based on a temperature of a thermo-electric cooler (TEC).

* * * * *

UNITED STATES PATENT AND TRADEMARK OFFICE
CERTIFICATE OF CORRECTION

PATENT NO. : 8,200,305 B2
APPLICATION NO. : 11/176578
DATED : June 12, 2012
INVENTOR(S) : In-duk Hwang It is certified that error appears in the above-identified patent and that said Letters Patent is hereby corrected as shown below:

Column 10, Line 64, In Claim 1, after "generating" insert -- a --.

Column 12, Line 57, In Claim 19, delete "varving" and insert -- varying --, therefor.

Signed and Sealed this
Fourteenth Day of August, 2012

David J. Kappos
*Director of the United States Patent and Trademark Office*